United States Patent [19]

d'Hondt et al.

[11] 4,359,555

[45] Nov. 16, 1982

[54] SALTS FORMED FROM FORMAMIDINES WITH POLYMERS CONTAINING SULFONIC ACID GROUPS

[75] Inventors: Christian d'Hondt, Riehen; Dieter Lohmann, Muttenz; Ernst Neuenschwander, Riehen, all of Switzerland

[73] Assignee: Ciba-Geigy Corporation, Ardsley, N.Y.

[21] Appl. No.: 160,529

[22] Filed: Jun. 18, 1980

[30] Foreign Application Priority Data

Jun. 29, 1979 [CH] Switzerland .......................... 6095/79
May 23, 1980 [CH] Switzerland .......................... 4053/80

[51] Int. Cl.$^3$ ............................ C08F 8/32; C08F 8/30
[52] U.S. Cl. ........................................ 525/358; 71/3; 525/374; 525/375; 525/379; 525/382
[58] Field of Search .................. 536/56; 525/344, 358, 525/375, 332, 333, 334, 335, 374, 379, 382; 528/171

[56] References Cited

U.S. PATENT DOCUMENTS 3,072,619  1/1963  Turbak ................................ 525/344
3,801,531  4/1974  Berejka .............................. 525/344

FOREIGN PATENT DOCUMENTS 978855   4/1961   United Kingdom .
1157742  9/1966   United Kingdom .
1394990  8/1972   United Kingdom .
1333078  10/1979  United Kingdom .

OTHER PUBLICATIONS

Toxicology 1, pp. 42-54, (1959).

Primary Examiner—C. A. Henderson
Attorney, Agent, or Firm—Frederick H. Rabin; John P. Spitals; Prabodh I. Almaula

[57] ABSTRACT

Salts of formamidines with polymers containing sulfonic acid groups; processes for producing these salts; and the use thereof in combating pests.

6 Claims, No Drawings

SALTS FORMED FROM FORMAMIDINES WITH POLYMERS CONTAINING SULFONIC ACID GROUPS

The present invention relates to salts formed from formamidines with polymers containing sulfonic acid groups, to processes for producing the salts, and to their use in combating pests.

The subject matter of the invention is thus salts having groups bound to side chains, which salts are formed from formamidines with polymers containing sulfonic acid groups, and correspond to the formula

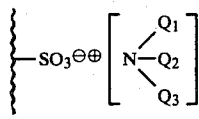
(I)

wherein $Q_1$ and $Q_2$ are each hydrogen, $C_1$–$C_4$-alkyl, or phenyl which is unsubstituted or substituted by $C_1$–$C_4$-alkyl or halogen, and $Q_3$ is

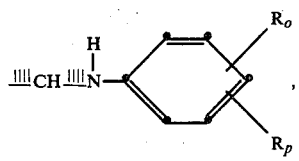

in which $R_o$ and $R_p$ are each hydrogen, halogen or $C_1$–$C_4$-alkyl, and wherein the groups of the formula I are bound either directly or by way of a bridge member, other than —$COOC_2H_4$—, to the polymer main structure, and wherein the proportion of recurring structural elements in the polymer having groupings in the formula I is at least 5% relative to the number of recurring structural elements of the polymer.

By halogen in the case of $Q_1$, $Q_2$, $R_o$ and $R_p$ are meant fluorine, chlorine, bromine or iodine, particularly however chlorine and bromine.

Examples of $C_1$–$C_4$-alkyl groups denoted by $Q_1$, $Q_2$, $R_o$ and $R_p$ are methyl, ethyl, propyl, isopropyl, n-, sec-, i- and t-butyl.

The polymers, which can be straight-chain, branched-chain or crosslinked, are for example: polyesters, polyester amides, polyamides, polyimides, polyamide imides, polyester imides, polyethers, polyurethanes, polyureas, polycondensation products of phenol, naphthalene, melamine and/or urea with aldehydes or ketones, such as formaldehyde, polysaccharides, gelatin, organopolysiloxanes, polyphosphacenes, polymers obtained by homo- or copolymerisation of monomers containing multiple compounds, for example C=C double bonds; or by ring-opening polymerisation of saturated or unsaturated aliphatic rings optionally containing hetero atoms. It is also possible to use tanning substances or polymers containing sulphonic acid groups, which are obtained by decomposition or transformation reactions from natural substances, such as cellulose, lignin or chitin, and the like.

The polymers can be straight-chain, branched-chain or crosslinked. If they are straight-chain polymers, they advantageously have a mean molecular weight of at least 500.

Preferred classes of straight-chain polymers are: straight-chain polymerisation products having a mean molecular weight of about 500 to about 2,000,000, especially of about 1000 to about 200,000; straight-chain polycondensation products having a mean molecular weight of about 500 to 60,000, particularly of about 1000 to about 30,000; straight-chain polyaddition products having a mean molecular weight of about 1000 to about 40,000, especially of about 2000 to about 20,000; straight-chain products which are obtained by ring-opening polymerisation and which have a mean molecular weight of about 500 to about 40,000, particularly about 1000 to about 20,000; decomposition and transformation products from natural substances having a mean molecular weight of about 500 to about 2,000,000, especially of about 1000 to about 100,000.

The mean molecular weights are determined by known methods, generally by means of vapour pressure osmometry, light scattering or viscosity measurement.

$Q_1$ is preferably hydrogen, methyl or n-butyl, $Q_2$ is methyl, and $Q_3$ is

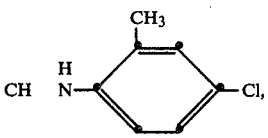

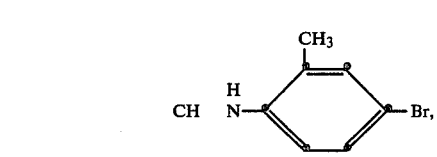

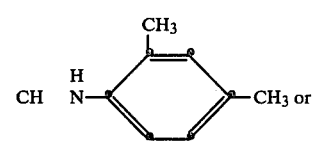

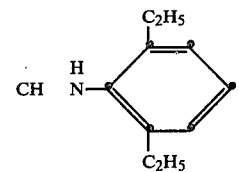

Of particular importance are polymers having the recurring structural elements of the formula II

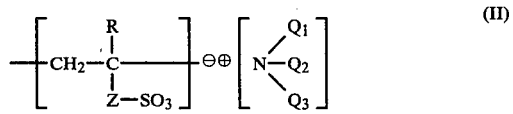
(II)

wherein $Q_1$, $Q_2$ and $Q_3$ have the meanings defined under the formula I, R is hydrogen, chlorine, —CN or $C_1$–$C_4$-alkyl, Z is the direct bond, —O—, straight-chain or branched-chain alkylene having 1–4 C atoms, phenylene or naphthylene each of which is unsubstituted or substituted by halogen atoms, alkyl or alkoxy groups having 1–4 C atoms or by a group —$SO_3$ M⊕, or Z is —$CH_2O$—$CH_2CH_2$—, —$CH_2OCH_2CH_2O$—, —$CH_2SCH_2CH_2$—, —$CH_2$—S—$CH_2CH_2O$—, a ring-substituted group

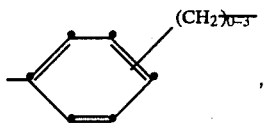

in which the ring is unsubstituted or is substituted by halogen atoms, or by alkyl or alkoxy groups having 1–4 C atoms, or Z is a group

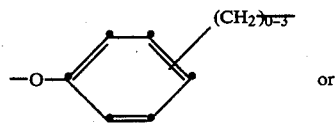

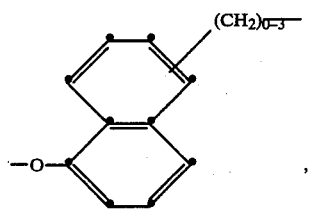

each of which is unsubstituted or substituted by —SO$_3$⊖M⊕, or Z is —COOR$_1$ or —CON(R$_2$)(R$_3$)—, in which R$_1$ is straight-chain or branched-chain C$_3$–C$_8$-alkylene which is unsubstituted or substituted by chlorine or bromine atoms, or interrupted by an oxygen atom, or R$_1$ is cyclohexylene, phenylene, naphthylene, naphthylene substituted by a group —SO$_3$⊖M⊕, or it is C$_2$–C$_4$-alkylene-O-phenylene or

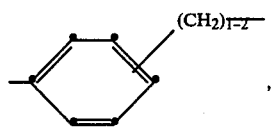

R$_2$ is the direct bond, straight-chain or branched-chain C$_1$–C$_6$-alkylene optionally interrupted by an oxygen atom, straight-chain or branched-chain oxyalkylene having 1–6 C atoms, phenylene, naphthylene, naphthylene substituted by a group —SO$_3$⊖M⊕, C$_1$–C$_4$-alkylene-O-phenylene,

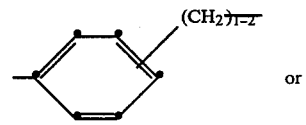

or

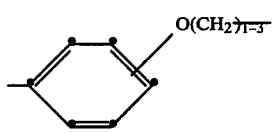

and R$_3$ is hydrogen or C$_1$–C$_6$-alkyl, and M⊕ is hydrogen or ⊕[N(Q$_1$)(Q$_2$)(Q$_3$)], the proportion of structural elemets of the formula II being at least 5%, preferably 30–100%, relative to the number of recurring structural elements of the polymer.

Preferred polymers of this type are: linear polymers having a mean molecular weight of about 500 to 2,000,000, which consist of recurring structural elements of the formula II and recurring structural elements of the formula III

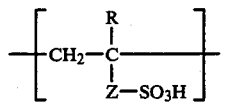

(III)

wherein R and Z have the above-given meanings, and the proportion of recurring structural elements of the formula III is 0.5 to 95% relative to the number of recurring structural elements of the polymer; polymers having recurring structural elements of the formula II, recurring structural elements of the formula IV

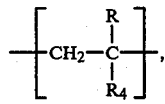

(IV)

wherein R is hydrogen, chlorine, —CN or C$_1$–C$_4$-alkyl, R$_4$ is hydrogen, halogen, —CON(R$_5$)(R$_6$), —COOH, —COO⊖Me⊕, phenyl which is unsubstituted or substituted by chlorine, or R$_4$ is alkyl, alkoxy or alkenyl each having up to 4 C atoms, cyclohexyl, —COO—alkyl having 1–12 C atoms in the alkyl moiety, —COO(CH$_2$)$_x$—OH, —COO-phenyl, —OCO—alkyl having 1–4 C atoms in the alkyl moiety, —OCO—phenyl, —CO—alkyl having 1–4 C atoms in the alkyl moiety, phenoxy or a group

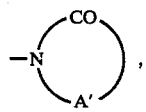

Me is a monovalent metal, x is an integer from 2–6 inclusive, A' is —(CH$_2$)$_3$—, —(CH$_2$)$_5$—, —CO—(CH$_2$)$_2$, —CO—CH=CH— or

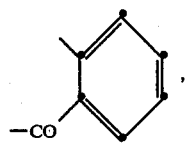

R$_5$ is hydrogen, C$_1$–C$_4$-alkyl, C$_1$–C$_6$-hydroxyalkyl or phenyl, and R$_6$ is hydrogen or C$_1$–C$_4$-alkyl, and optionally structural elements of the formula III, and the proportion of recurring structural elements of the formulae III and IV together is 0.5 to 95%, relative to the number of recurring structural elements of the polymer; cross-linked polymers having recurring structural elements of the formula II, recurring structural elements of the formula V,

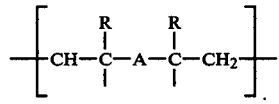

(V)

wherein R is hydrogen, chlorine, —CN or C$_1$–C$_4$-alkyl, A is the direct bond, —O—, —SO$_2$—,

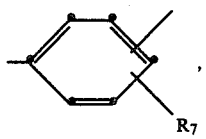

—COO—, —COOH$_2$—, —CONH—, —CONHCH$_2$—,
Me$^{2+}$($^-$OOC)$_2$—Me$^{3+}$($^-$OOC)$_2$

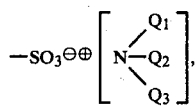

—CONH(CH$_2$)$_y$NHCO—, —COO(CH$_2$)$_x$—OCO—or
—COO(CH$_2$)$_2$[O—(CH$_2$)$_2$]$_{1-3}$OCO—, R$_7$ is hydrogen,
ethyl, —SO$_3$H or

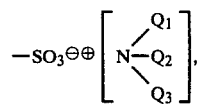

Me is a bi- or trivalent metal, y is an integer from 1–6 inclusive, and x is an integer from 2–6 inclusive, and Q$_1$, Q$_2$ and Q$_3$ have the above-given meanings, and optionally recurring structural elements of the formula III and/or IV, and the proportion of recurring structural elements of the formula V is 0.2–20%, and the proportion of recurring structural elements of the formula III and/or IV together is at most 94.5%, relative to the number of recurring structural elements of the polymer.

In the above formulae, alkyl and hydroxyalkyl groups denoted by R, R$_3$, R$_4$ and R$_5$, alkenyl groups denoted by R$_4$ as well as alkyl and alkoxy substituents in groups Z and R$_4$ can be straight-chain or branched-chain, but are preferably straight-chain. Alkyl groups R$_2$, R$_5$ and R$_6$ and alkyl or alkoxy substituents in groups Z preferably contain 1 or 2 C atoms. When Z groups are substituted by halogen atoms, they are in particular chlorine or bromine atoms. Alkylene groups R$_1$ and R$_2$ are preferably unsubstituted and contain 3–5 C atoms and 1–5 C atoms, respectively. Oxyalkylene groups R$_4$ and hydroxyalkyl groups R$_5$ advantageously contain 1–4 C atoms.

Examples of mono- to trivalent metals Me which may be mentioned are: Na, K, Ba, Mg, Ca and Al.

Particularly preferred polymers are those having recurring structural elements of the formulae II to V wherein R is hydrogen or methyl, Z is the direct bond, —COO—alkylene having 3–4 C atoms and especially phenylene, R$_1$ is alkylene having 2–4 C atoms, R$_2$ is —(CH$_2$)$_{2-4}$—, —C(CH$_3$)(CH$_3$)CH$_2$—, naphthylene and particularly phenylene each substituted by a group

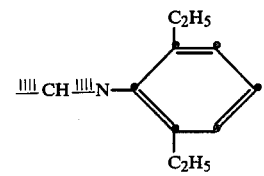

R$_3$ is hydrogen, R$_4$ is hydrogen, chlorine, unsubstituted phenyl, —CON(R$_5$)(R$_6$), —COO—alkyl having 1–8 C atoms in the alkyl moiety, —OCO—alkyl having 1 to 2 C atoms in the alkyl moiety, or alkoxy having 1–4 C atoms, R$_5$ and R$_6$ independently of one another are each hydrogen or methyl, A is the direct bond, —O—

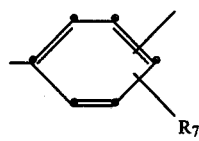

—COO—CH$_2$—, —CO—NH—CH$_2$—, —CONH(CH$_2$)$_y$NHCO—or —COO(CH$_2$)$_x$OOC—, y is an integer from 1–6 inclusive, x is an integer from 2–6, R$_7$ is hydrogen, —SO$_3$H or —SO$_3$$^\ominus$$^\oplus$[N(Q$_1$)(Q$_2$)(Q$_3$)], Q$_1$ is hydrogen, methyl or n-butyl, Q$_2$ is methyl and Q$_3$ is 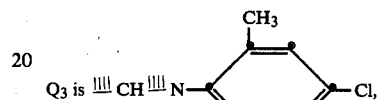

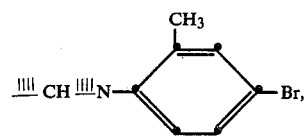

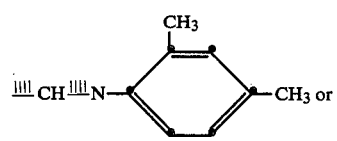

Very particularly preferred are salts of cations of the formulae

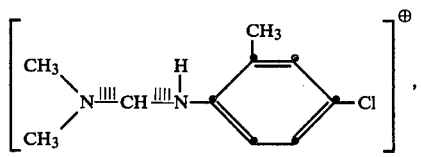

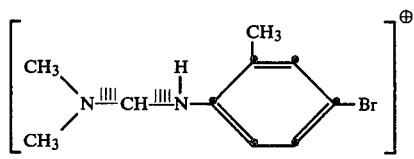

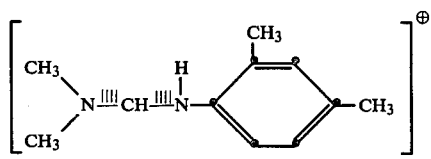

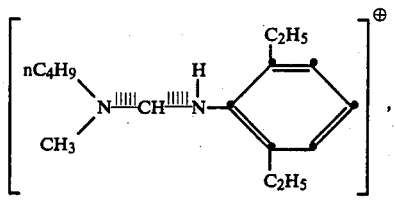

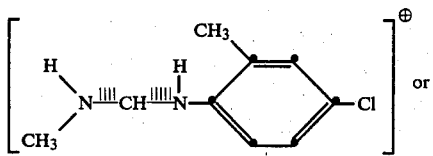

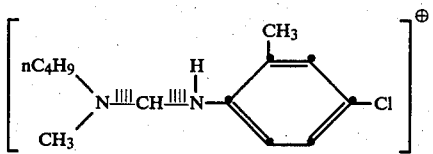

with anions of polyvinylsulfonic acids, polystyrenesulfonic acids, poly[N-(sulfoalkyl)-acrylamide] and sulfonated cation exchangers formed from styrene and about 8-12 percent by weight of divinyl benzene (crosslinking agent), of sulfonated cation exchangers having macroporous structures.

A further class of preferred polymers are those consisting of recurring structural elements of the formulae VIa to VIe.

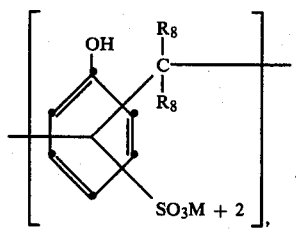
VIa

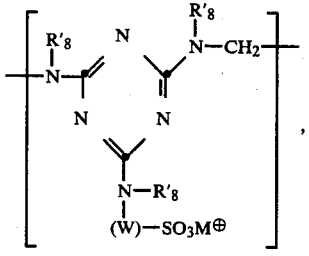
VIb

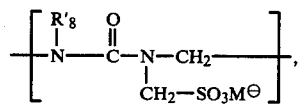
VIc

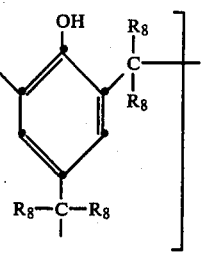
VId

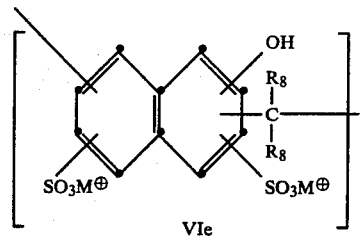
VIe or mixtures thereof, wherein $R_8$ is hydrogen or methyl

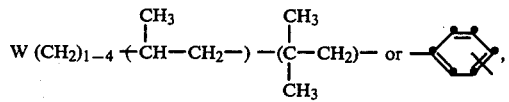

$R_8'$ is hydrogen or —$CH_3$, and $M^{\oplus}$ is hydrogen or a group $\oplus[N(Q_1)(Q_2)(Q_3)]$, and $Q_1$, $Q_2$ and $Q_3$ have the above-given meanings, and the proportion of structural elements of the formulae VIa, VIb, VIc and VIe, where $M^{\oplus}$ is other than hydrogen, is at least 5%, preferably 30-100%, relative to the number of recurring structural elements of the polymer.

Among the polymers having structural elements of the formulae II to VIe, those which have ion-exchanging properties have a particular importance. Polymer resins having a macroporous structure prove to be particularly suitable by virtue of their large internal surface and their high capacity for salt formation with the active substance, and by virtue of the adequate release of active substance under biological conditions.

Also preferred are straight-chain polycondensation products which have a mean molecular weight of about 500 to about 60,000 and which consist of recurring structural elements of the formula VII $$-[Y_1-L-Y_2-Q]- \quad (VII)$$

wherein L is a group

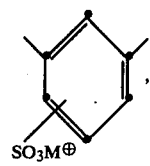

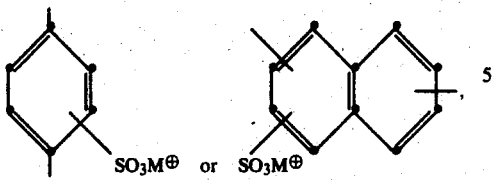

$z$ is the number 1 or 2, $z'$ is naught, 1 or 2, $M\oplus$ is hydrogen or a group $\oplus[N(Q_1)(Q_2)(Q_3)]$, $Y_1$ and $Y_2$ independently of one another are each —OCO—, —COO—, —CONH—, —NHCO—, —OCONH—,

or —NHCONH—, optionally branched-chain alkylene having 2–10 C atoms, or alkylene having 2–10 C atoms which is optionally interrupted by —O— or —NR$_8$—, or they are phenylene or naphthylene each of which is unsubstituted or is substituted by halogen atoms, methyl, methoxy or -SO$_3$M$\oplus$ groups, or they are cyclohexylene,

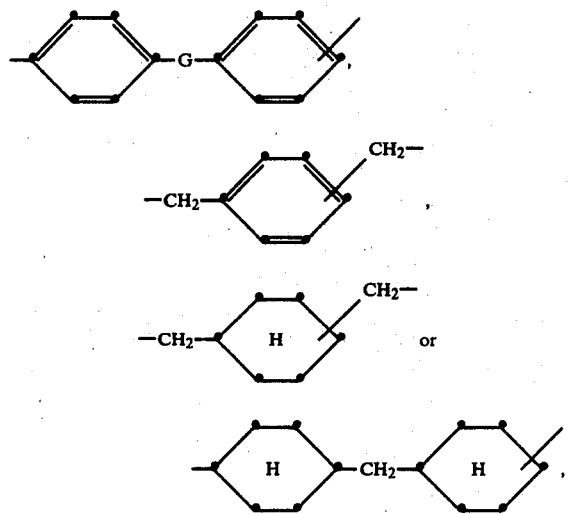

and G is the direct bond, -O-, —CH$_2$—,

or —SO$_2$—, and Q$_1$, Q$_2$ and Q$_3$ have the above-given meanings, and the proportion of structural elements of the formula VII, where M$\oplus$ is not hydrogen, is at least 5%, preferably 30–100%, relative to the number of recurring structural elements of the polymer.

The polymers according to the invention can be produced essentially by three methods known per say, namely (a) by reacting an optionally crosslinked or branched-chain polymer, which contains laterally bound —SO$_3$H groups, which are bound directly or by way of a bridge member different from —COOC$_2$H$_4$— to the polymer main structure, the proportion of these groups being at least 5% relative to the number of recurring structural elements of the polymer, with a compound of the formula VIII

  (VIII)

wherein Q$_1$, Q$_2$ and Q$_3$ have the meanings given under the forumla I;

(b) by firstly reacting a monomer, which contains -SO$_3$H- groups bound directly or by way of a bridge member different from —COOC$_2$H$_4$—, with a compound of the formula VIII, and subsequently converting the resulting monomer salt, optionally in the presence of comonomers and/or crosslinking agents, into a polymer, the molar ratio of monomer salt to comonomer and/or crosslinking agent being 1:19 to 1:0; or (c) by reacting a polymer, which contains reactive groups, for example the anhydride, acic chloride, ester, isocyanate or epoxide groups, with at least 5%, relative to the number of recurring structural elements of the polymer, of a compound of the formula IXa or IXb

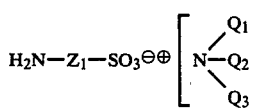  (IXa)

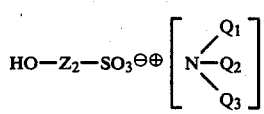  (IXb)

wherein Q$_1$, Q$_2$ and Q$_3$ have the meanings given in claim 1, Z$_1$ is the direct bond, straight-chain or branched-chain C$_1$-C$_8$-alkylene which is unsubstituted or substituted by chlorine or bromine or is optionally interrupted by an oxygen atom, or Z$_1$ is cyclohexylene, or phenylene or naphthylene each of which is unsubstituted or substituted by a group -SO$_3$ M$\oplus$, Z$_2$ is the direct bond, straight-chain or branched-chain C$_3$-C$_8$-alkylene which is unsubstituted or substituted by chlorine or bromine, or Z$_2$ is cyclohexylene, phenylene or naphthylene each unsubstituted or substituted by a group -SO$_3$ M$\oplus$, or Z$_2$ is

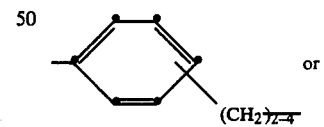  or

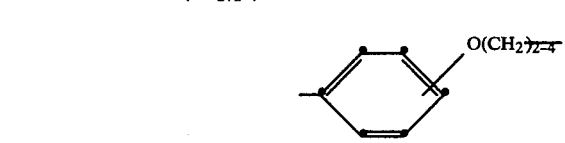, and M$\oplus$ is hydrogen or

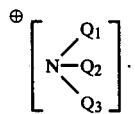.

The above reactions are performed advantageously in the presence of a suitable solvent, such as dioxane, chloroform, $CH_2Cl_2$, tetrahydrofuran, ethanol, methanol, and so forth. The reaction can be carried out in a homogeneous solution, in a dispersion or in a suspension. Salt formation is effected generally at a temperature between about 25° and 80° C. The fixation yield can be determined by customary analytical methods, such as by elementary analysis, thin-layer chromatography and gas-chromatography. The conversion of the monomer salts into the corresponding polymers and also the reaction of the salts of the formula IXa or IXb with the defined polymers according to process variant (c) are performed, depending on the type of monomer or polymer, for example by polymerisation, polycondensation or polyaddition, in a manner known per se and with the use of customary solvents, catalysts and/or polymerisation initiators.

Polymers having structural elements of the formula II are produced, using a process analogous to those described in the foregoing, (a) by reacting a polymer, which contains recurring structural elements of the formula III

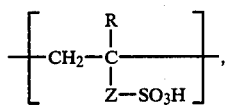 (III)

in a ratio of 20:1 to 1:1 relative to the number of recurring structural elements of the polymer, with a compound of the formula VIII, or (b) by firstly reacting a monomer of the formula IIa

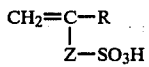 (IIa)

with a compound of the formula VIII, and then polymerising the resulting monomer salt of the formula IIb

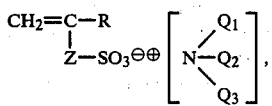 (IIb)

optionally in the presence of comonomers and/or crosslinking agents, the molar ratio of compounds of the formula IIb to comonomers and/or crosslinking agents being 1:19 to 1:0, and R, Z, $Q_1$, $Q_2$ and $Q_3$ having the meanings defined in the foregoing.

Polymers having a mean molecular weight of about 500 to about 2,000,000, which consist of recurring structural elements of the formula II and 0.5-95% of recurring structural elements of the formula III, can be produced by reacting a polymer consisting of recurring structural elements of the formula III, in a ratio of 20:1 to 100:99.5 relative to the number of recurring structural elements of the polymer, with a compound of the formula VIII; or by polymerising a monomer salt of the formula IIb, in a molar ratio of 1:19 to 199:1, with a comonomer of the formula IIa.

Polymers having a mean molecular weight of about 500 to 2,000,000, which consist of recurring structural elements of the formula II and all together 0.5 to 95% of recurring structural elements of the formula IV and optionally of recurring structural elements of the formula III, can be obtained by reacting a polymer consisting of recurring structural elements of the formula III and 0.5 to 95% of recurring structural elements of the formula IV, in a ratio of 20:1 to 100:99.5 relative to the number of recurring structural elements of the polymer, with a compound of the formula VIII; or by polymerising a salt of the formula IIb, in a molar ratio of 1:19 to 199:1, with a comonomer of the formula IVa

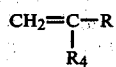

and optionally a comonomer of the formula IIa.

Finally, polymers consisting of recurring structural elements of the formula II, 0.5-20% of recurring structural elements of the formula V and optionally 75-94.5% of recurring structural elements of the formula III and/or IV can be produced either by reacting a polymer consisting of recurring structural elements of the formula III, 0.5-20% of recurring structural elements of the formula V and optionally 75-94.5% of recurring structural elements of the formula IV, in a ratio of 20:1 to 100:99.5 relative to the number of recurring structural elements of the polymer, with a compound of the formula VIII, or by polymerising a monomer salt of the formula IIb, in a molar ratio of 1:19 to 199:1, with a crosslinking agent of the formula Va

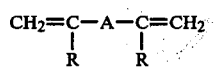 (Va)

and optionally a comonomer of the formula IVa and/or a comonomer of the formula IIa.

Polymers formed from recurring structural elements of the formulae VIa to VIe can be produced (a) by reacting a polymer consisting of recurring structural elements of the formulae VIa' to VIe'

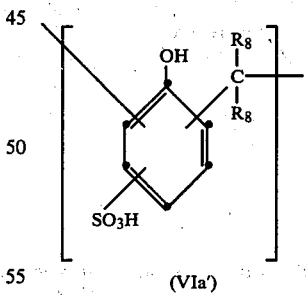

(VIa')

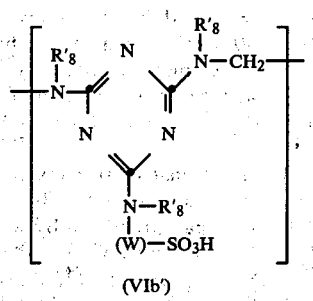

(VIb')

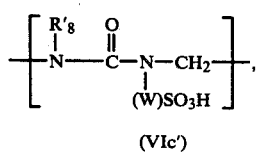

(VIc')

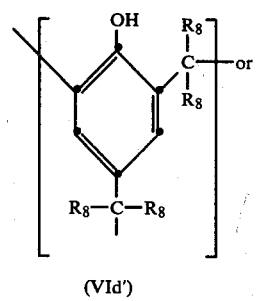

(VId')

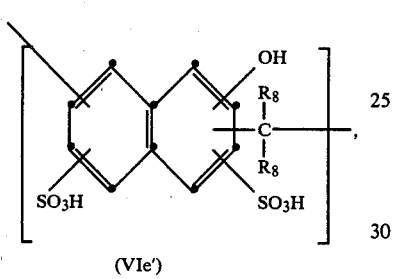

(VIe')

or of mixtures thereof, in a ratio of 20:1 to 1:1 relative to the number of recurring structural elements of the formulae VIa, VIb, VIc and VIe, with a compound of the formula VIII; or (b) by firstly reacting a compound of the formula VIa″, VIb″, VIc″ or VIe″

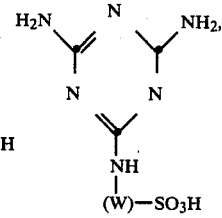

(VIa″)    (VIb″)

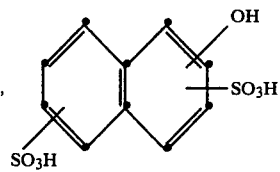

NH$_2$CO—NH—(W) SO$_3$H or,    (VIe″)

(VIc″)

or a mixture of such compounds, with a compound of the formula VIII, and subsequently polycondensing the resulting monomer salt of the formula VIa‴, VIb‴, VIc‴ or VIe‴

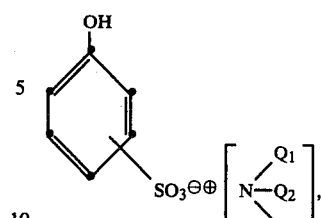

(VIa‴)

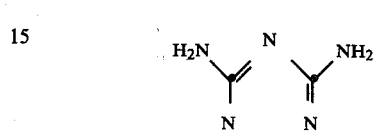

(VIb‴)

$H_2N-CO-NH-(W)-SO_3^{\ominus\oplus}$ 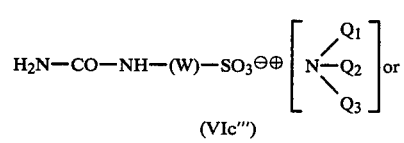 or (VIc‴)

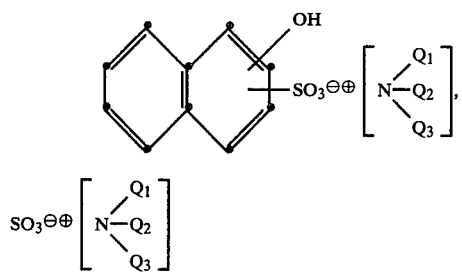

(VIe‴)

or the resulting mixture of such monomer salts, optionally in the presence of phenol and/or of a compound of the formula VIa″, VIb″, VIc″ or VIe″, with a compound of the formula X $$R_8-\underset{\underset{R_8}{|}}{C}=O, \qquad (X)$$

in which formulae the symbols Q$_1$, Q$_2$, Q$_3$, R$_8$ and (W) have the meanings defined in the foregoing, and the molar ratio of monomer salt of the formulae VIa‴, VIb‴, VIc‴ and/or VIe‴ to compound of the formulae VIa″, VIb″, VIc″, VIe″ and/or phenol is 1:19 to 1:0.

Polymers consisting of structural elements of the formula VII are advantageously produced (a) by reacting a polymer consisting of recurring structural elements of the formula VIIa $$-Y_1-L_1-Y_2-Q- \qquad (VIIa),$$

in a ratio of 20:1 to 1:1 relative to the number of recurring structural elements of the polymer, with a compound of the formula VIII; or (b) by firstly reacting a compound of the formula VIIb $$Y_3—L_1—Y_4 \qquad \text{(VIIb)}$$

with a compound of the formula VIII, and subsequently polycondensing or polyadding the resulting monomer salt of the formula VIIc $$Y_3—L_2—Y_4 \qquad \text{(VIIc)},$$

optionally in the presence of a compound of the formula VIIb, with a compound of the formula VIId $$Y_5—Q—Y_6 \qquad \text{(VIId)},$$

in which formulae the symbols have the followng meanings:

$L_1$ is a group

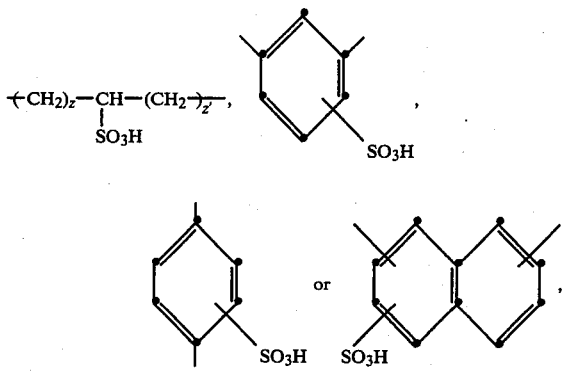

$L_2$ is a group

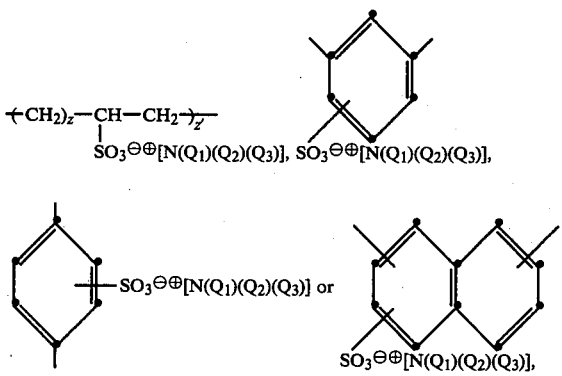

$Y_3$ and $Y_4$ independently of one another are each —OH, —NH$_2$, —COCl, —COOH, —COO—phenyl or —COO—alkyl having 1-3 C atoms in the alkyl moiety, and when $Y_3$ and/or $Y_4$ are —OH of NH$_2$, $Y_5$ and $Y_6$ independently of one another are each —COCl, —COOH, —COOP—phenyl, —COO—alkyl having 1-3 C atoms in the alkyl moiety or they are each —NCO, and, when $Y_3$ and/or $Y_4$ are —COCl, —COOH, —COO—alkyl having 1-3 C atoms in the alkyl moiety or —COOP—phenyl, $Y_5$ and $Y_6$ independently of one anotheer are each —OH or —NH$_2$, and $Y_1$, $Y_2$, Q, $Q_1$, $Q_2$ and $Q_3$ are as defined in the foregoing, and the molar ratio of compound of the formula VIIc to compound of the formula VIIb is 1:19 to 1:0.

The reactants to be used for the above reactions are known or can be produced by methods known per se. Polymers having laterally-bound —SO$_3$H groups bound as defined can be produced for example as follows:

(1) By introduction of the —SO$_3$H groups into an existing linear, branch-chain or crosslinked polymer chain by substitution, condensation or additon reactions, for example by sulfonation with SO$_3$, H$_2$SO$_4$, and the like, sulfochlorination, sulfomethylation, sulfoethylation with vinylsulfonic acids, sulfoalkylation with sulfones or sodium bisulfite addition reaction with double bonds, for example with polyethylene fumarate or butadiene-polymers; or by reaction of polymers having reactive groups, such as anhydride, acid chloride, ester, isocanate or epoxide groups, for example polyacrylic acid chloride, -methyl ester or -glycidyl ester, with functional sulfonic acids or functional polysulfonic acids which carry hydroxyl or amino groups, or by reaction of HO- or HN-containing polymers with cyclic sulfones.

(2) By synthesis of the polymer chain formed from monomers which contain the -SO$_3$H group in the free or masked form, for example as salt, whereby the polymer chain can be formed by polymerisation, polyaddition, polycondensation or ring-opening polymerisation, optionally in the presence of suitable comonomers and/or crosslinking agents. Examples for the formation of the polymer chain from suitable monomers are in particular the homo- and copolymerisation of polymerisable sulfonic acids, optionally in the presence of crosslinking agents, as described for example in the U.S. Pat. Nos. 2,983,712 and 2,914,499, and in the German Auslegeschriften (publication after examination) Nos. 1,224,506 and 1,292,129; polycondensation of diols, diamines, amino alcohols, dicarboxylic acids and derivatives thereof or diisocyanates, all containing sulfonic acid groups, with suitable Co-condensation components; and polycondensation of sulfonic acids of aromaic hydroxyl compounds, for example phenolsulfonic acids, with aldehydes or ketones, such as formaldehyde.

It is also possible to use a starting polymers sulfated or sulfoalkylated polysaccarides, such as cellulose, amylose, and so forth, ligninsulfonic acids or sulfoalkylated proteins, which can be produced in a manner known per se.

Examples of monomers to be used in process variant (b), as well as of comonomers and crosslinking agents to be if need be concomitantly used, are to be found in the above-mentioned U.S. Patent Specifications and German Auslegeschriften. Salts of the formulae IXa and IXb can be produced, using customary methods, by reaction of the appropriate amino- or hydroxysulfonic acids with compounds of the formula VIII.

The polymers having groups of the formula I are suitable for combating various pests on animals and plants.

The polymers containing groups of the formula I are particularly suitable for controlling all development stages, such as eggs, larvae, pupae and adults of insects, phytopathogenic and zooparasitic lice, mites and also ticks, for example of the orders: Lepidoptera, Coleoptera, Homoptera, Heteroptera, Diptera, Acarina, Thysanoptera, Orthoptera, Anoplura, Siphonaptera, Mallophaga, Thysanura, Isoptera, Psocoptera and Hymenoptera.

The polymers having groups of the formula I are especially suitable for combating insects which damage plants, in particular insects which damage plants by eating, in crops of ornamental plants and useful plants, especially in cottom crops (for example against *Spodoptera littoralis* and *Heliothis virescens*) and in crops of vegetables (for example against *Leptinotarsa decemlineata* and *Myzus persicae*), as well as for combating parasitic bee mites (*Varroa jacobsonii* and *Acarapis woodi*).

The polymers containing groups of the formula I surprisingly have a stability and long-term effect that are better than those of analogous salts known from the British Patent Specification No. 1,394,990. The compounds of the formula I are also safer in application than the free bases.

The polymers having groups of the formula I can be used on their own or together with suitable carriers and/or additives. Suitable additives can be solid or liquid and correspond to the substances common in formulation practice, such as natural or regenerated substances, solvents, dispersing agents, wetting agents, adhesives, thickeners, binders and/or fertilisers.

The compositions according to the invention are produced in a manner known per se by the intimate mixing and/or grinding of the polymers containing groups of the formula I with the appropriate formulation auxiliaries, optionally with the addition of dispersing agents or solvents which are inert to the active substances.

EXAMPLE 1

Production of polyvinylsulfonic acid and reaction thereof with
$N^1,N^1$-dimethyl-N-2-(4-chloro-o-tolyl)-formamidine (chlorodimeform) to form the salt.

By the method described by W. Kern and R.C. Schulz (Houben-Weyl, Methoden der organischen Chemie, Vol. 14/1, p. 1100), 291 g of sodium vinyl sulfonate, dissolved in 700 ml of water, are polymerised at about 5° C. with 2.4 g of potassium persulfate and 1 g of sodium hydrogen sulfite. The polymer is isolated by precipitation from the aqueous solution by the addition of 2.1 liters of methanol, and purified by reprecipitation from water/methanol.

To produce the free polyvinylsulfonic acid, 45 g of the sodium polyvinyl sulfonate obtained are dissolved in 115 ml of distilled water, and the solution is saturated at 0°–5° C. with gaseous hydrogen chloride. After removal of the sodium chloride which has precipitated, the solution is concentrated in a rotary evaporator, and is then freed from excess hydrogen chloride by repeated distillation with freshly added water. The polyvinylsulfonic acid obtained is isolated by freeze drying, and subsequently dried over phosphorus pentoxide under high vacuum.

27.2 g of the polyvinylsulfonic acid obtained are suspended in 300 ml of anhydrous chloroform, and the suspension is stirred with a solution of 49.4 g (0.264 mol) of chlorodimeform firstly for 10 hours at room temperature and then for 10 hours at 50° C. After cooling, the supernatant solution is decanted, and the product is freed by repeated digestion with chloroform from unreacted chlorodimeform. After pulverisation and drying, the yield is 61 g of beige-coloured product, which softens at about 110° C., contains 10.6 percent by weight of sulfur and 7.8 percent by weight of nitrogen, and has a mean molecular weight $\overline{M}_w$, calculated from a viscosity of $[\eta]=0.0075$ dl/g in chloroform at 20° C., of about 75,000. The content of chlorodimeform is about 54 percent by weight.

EXAMPLE 2

Production of polystyrenesulfonic acid and reaction thereof with chlorodimeform to give the salt.

By use of a method described by P. Schneider (Houben-Weyl, Methoden der organischen Chemie, Vol. 14/1, p. 683), 107 g of polystyrene ($\overline{M}_w$=about 200,000) are dissolved in 650 ml of dichloromethane, and a solution of 100 g of solid sulfur trioxide in 1350 ml of dichloromethane is slowly added at 0° C. with vigorous stirring and with cooling with dry ice/ethanol. The resulting suspension of sulfonated polystyrene is subsequently stirred at 0° C. for 43 hours, filtered, and then carefully washed with anhydrous diethyl ether. The white pulverulent, hygroscopic product is dried under high vacuum, and it contains 16.5 percent by weight of sulfur.

100 g of the polystyrene sulfonic acid obtained are slowly introduced into a solution of 90 g of chlorodimeform in 1000 ml of chloroform. After the exothermic reaction has subsided, stirring in maintained for 24 hours at room temperature. The product is filtered and subsequently washed with anhydrous diethyl ether until no further unreacted chlorodimeform can be detected. Drying under high vacuum yields a pulverulent white product having a softening point of about 194° C. and containing 5.8 percent by weight of nitrogen and 7.9 percent by weight of sulfur. The content of chlorodimeform is about 41 percent by weight.

EXAMPLE 3

In order to obtain a system free from water, a cation exchanger, which is produced by polymerisation of styrene with simultaneous crosslinking with 8 percent by weight of divinyl benzene and subsequent sulfonation ["Dowex HCR-S", Dow Chemical], is ground, and then dried at 90° C. in vacuo. The exchange capacity of the ion-exchanger is 4.7 m equiv. of -SO$_3$H/g.

150 g of chlorodimeform are dissolved in 561 g of Diesel oil, and 165 g of the dried and ground cation-exchanger are introduced portionwise into this solution. To the suspension obtained are added dropwise 24 g of methanol in the course of 15 minutes. An exothermic reaction commences, and the reaction mixture is held for 3 hours at 50° C. with continuous stirring. The liquid phase after this period of time contains no further chlorodimeform. To stabilise the suspension, 100 g of oleyl polyglycol ether and 10 g of bentone are stirred in. The stable suspension obtained contains per liter 150 g of chlorodimeform.

EXAMPLE 4

A cation exchanger, produced by polymerisation of styrene in the presence of 8 percent by weight of divinyl benzene and subsequent sulfonation ("Amberlyst 15", Röhm +Haas), and having an exchange capacity of 2.9 val./1, a particle size of 0.3–1.2 mm and a macro-reticular structure, is largely freed, before charging, from residual water by repeated mixing with dioxane and filtration (moisture content <1 percent by weight). 5 g (0.025 mol) of chlorodimeform, dissolved in 4.14 g of dioxane, are subsequently added to 5 g of the cation-exchanger resin and 5.86 of dioxane. The reaction mixture is heated with stirring to 60° C., and after one hour, a small amount of the supernatant solution is taken for the purpose of analysis of the active substance by gas-chromatography. The heating is turned off after 8 hours, and 24 hours after commencement of the charging process, a second analysis specimen is taken. The total reaction time is 31 hours. The reaction mixture is filtered by means of a Büchner funnel, and washed four times with 50 ml of acetone each time. The ion-exchanger resin charged with chlorodimeform is subsequently dried at room temperature until the weight is constant. The content of chlorodimeform in the ion-exchanger resin is calculated from the drop in concentration in the supernatant solution. The initial concentration of the solution is 33.3 percent by weight (5 g of chlorodimeform in 10 g of dioxane). After a reaction time of one hour, the concentration is 23.8 percent by weight, and after one day it is 18.7 percent by weight. From that is obtained a calculated content of chlorodimeform in the charged ion-exchanger of 35 percent by weight. In order to confirm this value, a chlorine and nitrogen elementary analysis is performed.

| calculated | Cl 6.3% | N 4.9% |
|---|---|---|
| found | Cl 6.4% | N 5.2% |
| | (average of 6.2 and 6.6%) | (average of 5.3 and 5.1%) |

From the nitrogen content there is given a calculated value of 36.5 percent by weight of chlorodimeform, and from the chlorine content a calculated value of 35.5 percent by weight of chlorodimeform, values which agree very well with the expected (theoretical) value of 35 percent by weight.

The ion-exchanger pellets charged with chlorodimeform are subsequently ground to a fine powder. The chlorodimeform content in the charged ion-exchanger is checked by another method:

10 ml of chloroform, which contains 0.25 percent by weight of eicosane as international standard for gas-chromatographical analysis and 0.5 ml of diethylamine, are added to 150 mg of the ion-exchanger charged with chlorodimeform. In this way the chlorodimeform on the ion-exchanger is to be exchanged by the stronger base, diethylamine, and the content of released chlorodimeform to be then measured according to the gas-chromatogram. After a reaction time of one day, a specimen of the chloroform solution is examined with respect to the chlorodimeform content in comparison with that of a standard solution of 50 ml of chlorodimeform in 10 ml of chloroform containing 0.25 wt. % of eicosane as international standard for gas-chromatographical analysis. From this analysis is obtained a calculated content of chlorodimeform in the ion-exchanger of 34 percent by weight. This value is in good agreement both with the value obtained by elementary analysis and with the value given from the drop in concentration during the charging of the resin (35%).

In an analogous manner, a cation-exchanger resin, produced by polymerisation of styrene in the presence of 8% of divinyl benzene and subsequent sulfonation (wt. % of S), was charged with the following active substances:

| Compound No. | |
|---|---|
| I | $N^1$—methyl-$N^2$—(4-chloro-o-tolyl)-formamidine, |
| II | $N^1$—$N^1$—dimethyl-$N^2$—(4-bromo-o-tolyl)-formamidine, |
| III | $N^1$—methyl-$N^1$—n-butyl-$N^2$—(4-chloro-o-tolyl)-formamidine, |
| IV | $N^1$—methyl-$N^1$—n-butyl-$N^2$—(2,6-diethylphenyl)-formamidine, |
| V | $N^1$—$N^1$—dimethyl-$N^2$—(2,4-dimethylphenyl)-formamidine. |

The results are summarised in the following Table I.

TABLE I

| Compound No. | Initial concentration of the solution wt. % | Concentration of the solution after 1 h, wt. % | Concentration of the solution after 1 day, wt. % | Calculated charge wt. % | Charge according to elementary analysis wt. % | Charge after exchange with diethylamine wt. % |
|---|---|---|---|---|---|---|
| I | 31.5 | 20.6 | 19 | 31 | 29.5 | 32 |
| II | 37.9 | 25.2 | 23 | 38.3 | 35.1 | 37 |
| III | 37.5 | 26.6 | 26.6 | 32.5 | 34.1 | 33 |
| IV | 38.3 | 31 | 27.5 | 32.5 | 33.9 | 32.5 |
| V | 30.5 | 16.8 | 15.7 | 33.7 | 32.4 | 33 |

EXAMPLE 5

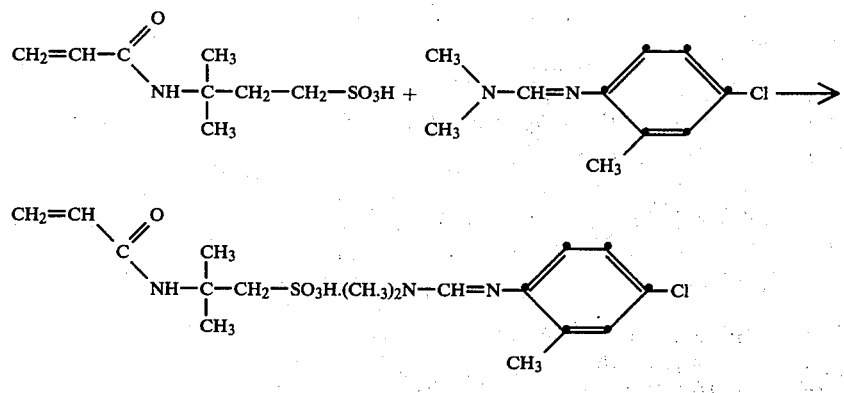

Monomeric salt from chlorodimeform and 2-acrylamido-2-methylpropanesulfonic acid A solution of 19.6 g (0.1 mol) of chlorodimeform in 250 ml of methanol is slowly added dropwise at room temperature, in the course of 45 minutes, to a suspension of 20.7 g (0.1 mol) of 2-acrylamido-2-methylpropanesulfonic acid in 400 ml of methanol. After the slightly exothermic reaction has subsided, stirring is continued for 6 hours at room temperature. The resulting clear solution of the chlorodimeform salt is concentrated by evaporation in a rotary evaporator, and the residue is stirred up with 500 ml of anhydrous ether. The white suspension obtained is filtered, and the residue is again treated with 200 ml of anhydrous ether. Filtration and subsequent drying under high vacuum yield the salt in the form of a white crystalline solid product, which slowly decomposes on melting in the range of 110°–114° C.

Yield: 39.4 g = 97.7% of theory

Analytical composition: $C_{17}H_{26}N_3O_4S$ Cl: calculated: C = 50.55 H = 6.49 N = 10.40 S = 7.94 Cl = 8.78%, found: C = 50.18 H = 6.24 N = 10.45 S = 7.93 Cl = 8.86.

EXAMPLE 6

Polymerisation of the monomer salt formed from chlorodimeform and 2-acrylamido-2-methylpropanesulfonic acid

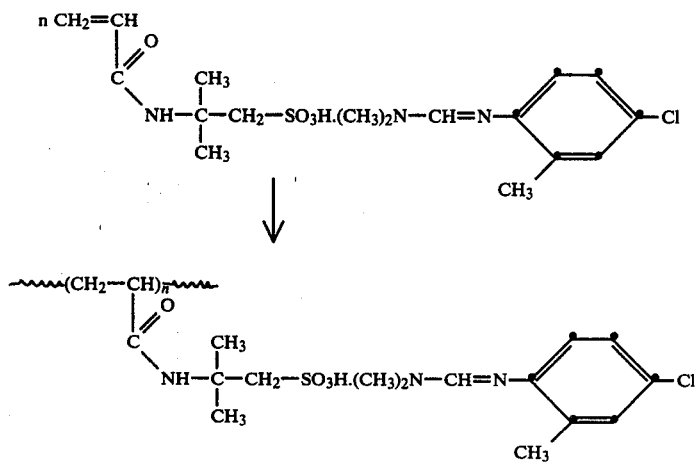

with azo-isobutyronitrile (AiBN) in N,N-dimethylacetamide (DMA).

(a) 2 g (0.01 mol) of chlorodimeform are dissolved in 10 ml of anhydrous DMA, and a solution of 2.07 g (0.01 mol) of 2-acrylamido-2-methylpropanesulfonic acid in 10 ml of anhydrous DMA is added. The formed solution of the chlorodimeform salt is stirred for 6 hours at room temperature with the passing through of dry nitrogen, and is subsequently polymerised, with the addition of 40 mg of AiBN, at 55°–60° C. for 15 hours. The formed polymer is isolated by precipitation in the reaction solution by the addition of 300 ml of anhydrous diethyl ether. After filtration, washing 3 times with 50 ml of anhydrous ether each time, and drying under high vacuum, the yield is 3.8 g of white pulverulent material, which on melting slowly decomposes above 100° C.; yield: 94% of theory.

molecular weight:

elementary analysis: calculated: C 50.5, H 6.5, N 10.4, S 7.9, Cl 8.8%: found: C 49.8, H 6.7, N 10.4, S 7.5, Cl 8.3%.

The H-NMR spectrum of the product in DMSO-$d_6$ no longer shows the multiplets in the region of 5.3–6.1 ppm which are characteristic for the monomer salt.

(b) In an analogous manner, 4.03 g (0.01 mol) of the monomer salt produced according to Example 5 are dissolved in 20 ml of anhydrous DMA, and then polymerised under $N_2$ at 55°–60° C. with AiBN. The product obtained corresponds in structure and composition to the polymer produced under (a).

EXAMPLE 7

Insecticidal stomach-poison action

Cotton plants were sprayed with an 0.02% (relative to the active substance) aqueous suspension (obtained from a 25% wettable powder, or from a 20% suspension). After the drying of the coating, the cotton plants were each infested with Spodoptera littoralis larvae in the $L_1$ stage. The test was carried out at 30°–35° C. with 60% relative humidity.

Compounds according to Examples 1–6 exhibited in the above test a good insecticidal stomach-poison action against Spodoptera littoralis larvae.

EXAMPLE 8

Acaricidal action

Phaseolus vulgaris plants were infested, 12 hours before the test for acaricidal action, with an infested piece of leaf from a mass culture of Tetranychus urticae. The transferred mobile stages were sprayed with the suspended test preparations from a chromatography-sprayer in a manner ensuring no overflow of the spray liquor. An assessment was made after two and seven days, by examination under a binocular microscope, of the living larvae and dead larvae, adults and eggs, and the results were expressed as percentages. The treated plants were kept during the "holding time" in greenhouse compartments at 25° C.

Compounds according to Examples 1–6 inclusive were effective in the above test against adults, larvae and eggs of Tetranycus urticae.

What is claimed is:

1. A salt of an anionic polymer selected from the group consisting of polystyrenesulfonic acid, copolymers of polystyrenesulfonic acid, polyvinylsulfonic acid and poly-[N-(sulfoalkyl)acrylamide] wherein the cation of said salt is of the formula

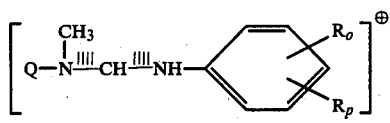

in which Q is hydrogen, alkyl of 1 to 4 carbon atoms, phenyl, or phenyl substituted with alkyl of 1 to 4 carbon atoms or halo, and each of $R_o$ and $R_p$ is hydrogen, halo or alkyl of 1 to 4 carbon atoms.

2. A salt according to claim 1 wherein said polymer contains a plurality of units of the formula

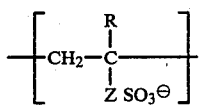

wherein R is hydrogen or methyl and Z is a direct bond or phenylene.

3. A salt according to claim 1 wherein Q is hydrogen, methyl or butyl, $R_o$ is alkyl and $R_p$ is alkyl, chloro or fluoro.

4. A salt according to claim 3 wherein $R_o$ is methyl in the 2-position and $R_p$ is chloro, bromo or methyl in the 4-position.

5. A salt according to claim 3 wherein $R_o$ and $R_p$ are each ethyl in the 2- and 6-positions.

6. A salt according to claim 5 wherein said polymer is polyvinyl sulfonic acid, sulfonated polystyrene or a sulfonated copolymer of styrene and divinyl benzene and said cation is selected from the group consisting of
$N^1$-methyl-$N^2$-(4-chloro-o-tolyl)formamidine,
$N^1$-$N^1$-dimethyl-$N^2$-(4-bromo-o-tolyl)formamidine,
$N^1$-methyl-$N^1$-n-butyl-$N^2$-(4-chloro-o-tolyl)formamidine,
$N^1$-methyl-$N^1$-n-butyl-$N^2$-(2,6-diethylphenyl)formamidine,
$N^1$-$N^1$-dimethyl-$N^2$-(2,4-dimethylphenyl)formamidine.

* * * * *